United States Patent [19]
Picataggio et al.

[11] Patent Number: 5,798,237
[45] Date of Patent: Aug. 25, 1998

[54] RECOMBINANT LACTOBACILLUS FOR FERMENTATION OF XYLOSE TO LACTIC ACID AND LACTATE

[75] Inventors: Stephen K. Picataggio, Golden; Min Zhang, Lakewood; Mary Ann Franden, Littleton; James D. Mc Millan, Boulder; Mark Finkelstein, Fort Collins, all of Colo.

[73] Assignee: Midwest Research Institute, Kansas City, Mich.

[21] Appl. No.: 541,632

[22] Filed: Oct. 10, 1995

[51] Int. Cl.$^6$ .............. C12P 7/56; C12N 1/20; C12N 15/00; C12N 1/00
[52] U.S. Cl. .............. 435/139; 435/252.3; 435/752.9; 435/320.1; 435/243; 435/248
[58] Field of Search .............. 435/252.3, 252.9, 435/320.1, 139, 243, 248

[56] References Cited

PUBLICATIONS

McMillan, J., *Conversion of Hemicellulose Hydrolyzates to Ethanol*, Chapter 21, Enzymatic Conversion of Biomass for Fuels Production, in ACS Symposium Series 566, pp. 411–437, 1994.
Chassy, 1985, *Trends in Biotechnol.*3; 273–275.
Kandler, O. 1983, *Antonie van Leeuwenhoek*, 49, 209–244.
Gold et al., 1992, *J. Industrial Microbiol.*, 10, 45–54.
Olsson et al., 1992, *Appl. Biochem. Biotechnol.*, 34/35, 359–368.
Barre, P. 1978, *Journal of Applied Bacteriology* 44: 125–129.
Posno et al., 1991, *App. Environ. Microbiol.*, 57, 2764–2766.
Bradford, M., *Anal. Biochem.* (1976) 72:248.
Schief, R.F. and Wensink, P.C., *Practical Methods in Molecular Biology*, Enzyme Assays, pp. 46–50.
Menezes et al., 1990, *Indin Journal of Biochemistry & Biophysics* 27:18–22.
Posno et al. 1991, *Appl. Environ. Microbiol.* 57:1822–1828.
O'Sullivan and Klaenhammer, 1993, *Applied and Environmental Microbiology*, 59: 2730–2733.
Lokman et al. 1994, *Mol. Gen. Genet.* 245: 117–125.
Leer et al., 1992, *Gen. Genet.* 234: 265–274.
Thompson, K. and Collins, M. 1991, *Appl. Microbiol. Biotechnol.*, 35, pp. 334–338.
Lokman et al., Mol. Gen. Genet., 230(1–2) 1991, 161–169.
Kreuzer et al., J. Bacteriol. 171: 3840–3845 (1989).

*Primary Examiner*—George C. Elliott
*Assistant Examiner*—Andrew Wang
*Attorney, Agent, or Firm*—Edna M. O'Connor; Ken Richardson; Ruth Eure

[57] ABSTRACT

A recombinant Lactobacillus MONT4 is provided which has been genetically engineered with xylose isomerase and xylulokinase genes from *Lactobacillus pentosus* to impart to the Lactobacillus MONT4 the ability to ferment lignocellulosic biomass containing xylose to lactic acid.

12 Claims, 4 Drawing Sheets

*Lactobacillus* MONT4 in 2% Xylose

RECOMBINANT LACTOBACILLUS FOR FERMENTATION OF XYLOSE TO LACTIC ACID AND LACTATE

CONTRACTUAL ORIGIN OF THE INVENTION

The United States Government has rights in this invention under Contract No. DE-AC36-83CH10093 between the United States Department of Energy and the National Renewable Energy Laboratory, a Division of Midwest Research Institute.

FIELD OF THE INVENTION

This invention relates to a microorganism which has been genetically altered to permit fermentation of xylose to lactic acid and lactate.

BACKGROUND OF THE INVENTION

Lactic acid, and its salt known as lactate, are commercially viable products useful in various fields including medicine and food processing. Currently, lactic acid is commercially produced from cornstarch or sucrose. Lignocellulosic biomass offers a favorable alternative as a feedstock for the biological production of lactic acid because it is readily available, has no competing food value, and is less expensive than either cornstarch or sucrose. Theoretically, a microorganism would be able to ferment the sugars contained in the biomass to lactic acid. However, several obstacles preclude efficient utilization of this feedstock by a microorganism for lactic acid production. Lignocellulosic feedstocks are largely comprosed of cellulose, hemicellulose and lignin. While several micro-organisms can efficiently ferment the glucose component in cellulose, conversion of the pentose sugars contained in the hemicellulose fraction has proven more difficult. The most abundant pentose sugars in hemicellulose include xylose and arabinose. Fermentation of xylose and arabinose remains a primary obstacle for economical biomass conversion. The few microorganisms that can grow on both pentose and hexose sugars in lignocellulosic feedstocks typically grow slowly and demonstrate marginal yields and productivities. Because the cost of feedstock can represent more than 20% of all process costs, an economical biomass conversion process critically depends upon the rapid and efficient conversion of essentially all of the sugars present in both the cellulose and hemicellulose fractions. Therefore, an expanded substrate utilization range which includes efficient conversion of both hexose and pentose sugars is an important requirement of such a microorganism.

In addition to an expanded substrate utilization range, such a microorganism will be required to tolerate and perform at varying process conditions including elevated temperature, low pH, and high salt concentration. Previous studies have shown that most microorganisms demonstrate relatively poor pentose sugar fermentation performance on dilute-acid hydrolyzates compared to laboratory formulations containing pure sugars (McMillan, J., *Conversion of Hemicellulose Hydrolyzates to Ethanol*, Chapter 21, Enzymatic Conversion of Biomass for Fuels Production, in ACS Symposium Series 566, pp. 411–437, 1994). The lower conversion yield and productivity from dilute-acid hydrolyzates have been attributed to the presence of inhibitory compounds such as acetic acid, furfurals and assorted phenolics. Therefore, in addition to fermenting under ranging process conditions the variety of sugars found in lignocellulosic biomass, the microorganism must also be able to efficiently ferment biomass-derived sugars in the presence of these inhibitory components. The present invention provides a microorganism with these desirable characteristics and abilities.

Lactobacillus are used commercially in the preparation of a variety of food and feed products (Chassy, *Trends in Biotechnol.*, 3, pp. 273–275, 1985) providing several potential advantages for biomass conversion. Lactobacillus are gram-positive, non-spore-forming bacteria capable of fermenting many of the carbohydrates commonly found in lignocellulosic biomass, such as glucose, starch, cellobiose, lactose, xylose, arabinose and ribose, and produce high concentrations of lactate (Kandler, O., *Antonie van Leeuwenhoek*, 49, pp. 209–244, 1983; Gold et al., *J. Industrial Microbiol.*, 10, pp. 45–54, 1992). The fermentations may be conducted at low pH and elevated temperatures, thus allowing the use of process conditions which minimize contamination. Lactobacillus show considerable resistance to the inhibitory compounds found in dilute-acid hydrolyzates (Olsson et al., *Appl. Biochem. Biotechnol.* 34/35, pp. 359–368, 1992). In addition, many Lactobacillus are Generally Recognized As Safe (GRAS) for use at industrial scale.

Pentose sugars, such as xylose and arabinose, are readily fermented by facultative heterofermentative strains to equimolar amounts of lactate and acetate via the phosphoketolase pathway. However, glucose and xylose consumption rates are relatively low compared to other fermentative microorganisms (Olsson et al., supra). In contrast, obligate homofermentative strains of Lactobacillus can ferment glucose to lactate as the sole fermentation product at over 95% of the maximum theoretical conversion yield (Gold et al., supra). Catabolism occurs via glycolysis, converting 1 mol of hexose to 2 mol of lactic acid. Unfortunately, these strains are incapable of fermenting pentose sugars. A survey of 31 different Lactobacillus strains identified several that were capable of at least 90% conversion of glucose, cellobiose, lactose or starch to a mixture of lactic acid, ethanol and acetic acid (Gold et al., supra). No strains were found that were able to convert xylose at similar efficiency.

Lactobacillus MONT4, originally isolated from high-temperature fermenting grape musts (Barre, P., *Journal of Applied Bacteriology*, 44, pp. 125–129, 1978), is unique in that it ferments L-arabinose and D-ribose exclusively to lactic acid by a homofermentative metabolic pathway unknown among other lactobacilli, which typically ferment pentose sugars via the heterofermentative phosphoketolase pathway. Lactobacillus MONT4 is further distinguished from other homofermentative lactobacilli, such as *L. amylovorous*, *L. delbrueckii*, *L. farciminis*, *L. helviticus* and *L. salivarius*, by its unique sugar utilization pattern. Whereas Lactobacillus MONT4 can ferment arabinose, it is incapable of fermenting the xylose commonly found in lignocellulosic feedstocks. Thus far, the xylose operon from *Lactobacillus pentosus* has been cloned and expressed only in other heterofermentative lactobacilli (Posno et al., *Appl. Environ. Microbiol.* 57, pp. 2764–2766, 1991). Attempts to transform thermophilic lactobacilli have been largely unsuccessful. (Thompson, K. and Collins, M., *Appl. Microbiol. Biotechnol.*, 35, pp.334–338, 1991).

All references cited in this patent application are incorporated herein by reference.

SUMMARY OF THE INVENTION

It is an object of the present invention to provide a homofermentative strain of Lactobacillus MONT4 capable of fermenting pentose sugars including xylose and arabinose at near theoretical yield. This is an ideal microorganism for economical lactate production from renewable biomass substrates.

It is a further object of the present invention to provide a method for producing lactic acid from hemicellulose hydrolyzates of lignocellulosic biomass.

This invention relates to a Lactobacillus MONT4 strain that has been metabolically engineered for xylose fermentation by introducing the xylose isomerase and xylulokinase genes that link xylose assimilation to its homofermentative glycolytic pathway. This engineered strain produces lactate as the sole fermentation product from xylose at near-theoretical yield (about 1.67 moles lactate/mole xylose) and has potential commercial application for lactic acid and lactate production from lignocellulosic feedstocks because it also ferments many of the other sugars commonly found in these feedstocks, including glucose, cellobiose, mannose and arabinose.

DESCRIPTION OF THE PREFERRED EMBODIMENTS

Figure 1A:
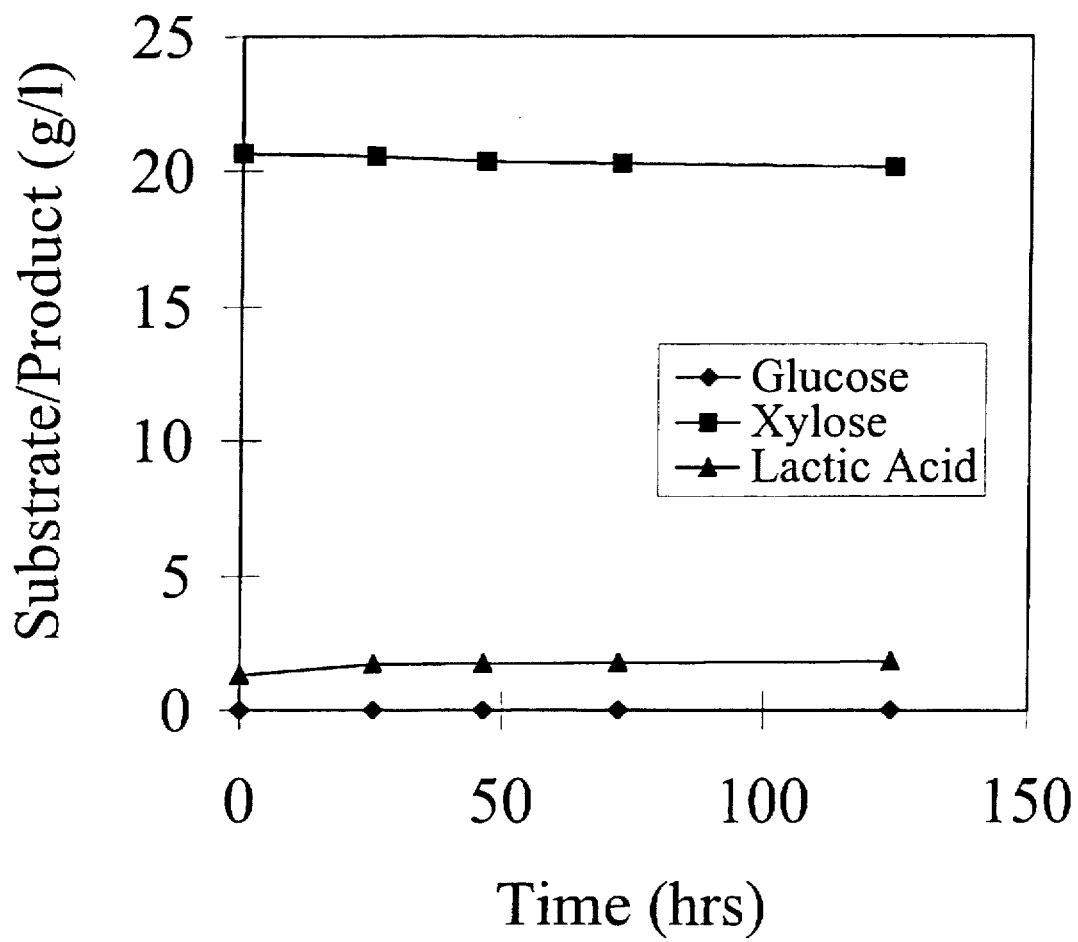
FIG. 1 sets forth data comparing the lactic acid fermentation performance of transformed and untransformed MONT4 on xylose and xylose plus glucose.

The invention is a recombinant Lactobacillus with an expanded substrate utilization range which is capable of growth on and/or efficient lactic acid production from xylose or other pentoses, as well as hexoses, as its sole carbon source.

The microorganisms used to prepare the present invention are those which are capable of being genetically altered to produce the necessary enzymes to form a metabolic pathway for catabolizing pentoses, particularly xylose. The microorganism may naturally have some enzymes in the pathway but will not be able to ferment xylose into lactic acid until it has been genetically altered. The manner of genetic alteration may use any combination of known genetic engineering techniques such as mutation or addition of foreign DNA, provided that the microorganism is able to ferment xylose to lactic acid after treatment Foreign DNA may be introduced into the microorganism by any conventional technique such as conjugation, transformation, transduction or electroporation.

Many microorganisms which are capable of fermenting sugars to lactic acid lack at least one of the genes for the enzymes which make up a metabolic pathway for converting xylose and other pentoses into lactic acid. Exogenous genes may be added to complete a metabolic pathway. One need not add genes necessary for every step if the host microorganism already produces an enzyme in the pathway. The number of genes to be added will depend on the starting microorganism.

The indigenous Lactobacillus genes may be altered by any known genetic manipulation technique to provide a protein with the necessary enzyme activity to produce the desired metabolic pathway. The altered genes may complement one or more of the introduced genes from another organism to complete the metabolic pathway. The use of this procedure may be advantageous by reducing the number of genes one needs to add to the host cell.

Sufficient genes may be added so that the recipient microorganism may ferment xylose as the sole carbon source. The microorganism may or may not be able to multiply on xylose as the sole carbon source but may be capable of fermenting xylose to lactic acid.

A gene may be added to a cell by way of a vector. The vector may be in the form of a plasmid, cosmid or virus which is compatible with the cell's DNA and any resident plasmids. Generally, vectors either integrate into the recipient microorganism's DNA or the vector has an origin of replication to stably maintain the vector throughout many microbial generations. The origin of replication may code for either stringent or non-stringent replication.

To express the gene(s), a structural gene is generally placed downstream from a promotor region on the DNA. The promotor must be recognized by the recipient microorganism. In addition to the promotor, one may include, delete or modify regulatory sequences to either increase expression or to control expression. Expression may be controlled by an inducer or a repressor so that the recipient microorganism expresses the gene(s) only when desired.

In a preferred embodiment of the invention, xylose metabolic pathway genes are obtained from xylose metabolizing microorganisms and added to microorganisms which do not otherwise ferment xylose to lactic acid. As an example, the xylose metabolizing genes from *Lactobacillus pentosus* are added to Lactobacillus MONT4.

In other preferred embodiments of the present invention, a genetic element comprising two genes enabling xylose metabolism may be placed on the same vector. The genes on a vector may be in any order, grouping or orientation relative to each other. The expression of the genes and the resulting functional activity of their corresponding gene products represent a new biochemical pathway that links xylose metabolism to the Pentose Phosphate and Embden-Meyerhof Parnas pathways in Lactobacillus, conferring upon these cells, for the first time, the ability to grow on and ferment xylose directly to lactate.

The microorganism according to the present invention may be mixed with any xylose, arabinose or other pentose sugar containing medium and allowed to ferment the medium to produce lactic acid. The medium may include other fermentable sugars, such as glucose. If microbial growth is desired, other nutrients which are necessary for microbial growth may be added and the microorganism allowed to reproduce.

Efficient transport of the pentoses into Lactobacillus may be through native Lactobacillus transport proteins, mutated Lactobacillus transport proteins, or through the addition of new facilitated transporters introduced by cloning new transport genes into Lactobacillus with or without mutagenesis of the cloned transport genes.

The step of microbial growth may be separate from fermentation. Xylose, arabinose and other pentoses, or mixtures thereof may be used as a carbon source for microbial growth or one can separately culture the microorganism on any medium (with or without a pentose) until sufficient numbers of microorganisms are present as a first step and then a pentose containing medium is added for fermentation in a second step. If a two step method is used, one may control expression of the genes in the new metabolic pathway so that greater expression occurs during the second step.

The choice of substrates will depend on cost and supply of the substrate to be fermented to lactic acid. A typical low-cost supply of pentoses is from hemicellulose. Xylose, arabinose and other pentoses are liberated from hemicellulosic materials by treatment with steam and/or an acid or alkali. Smaller amounts of other sugars such as glucose are also separated during this treatment and are also fermented by Lactobacillus to lactic acid.

When the substrate is cellulosic materials, the cellulose may be hydrolyzed to sugars simultaneously or separately and also fermented to lactic acid. Since hemicellulose is generally easier to hydrolyze to sugars than cellulose, it is preferable to first prehydrolyze the hemi-cellulosic material, separate the soluble pentose sugars and then hydrolyze the cellulose by treatment with steam and/or acid or alkali or cellulases to form glucose. Both pentose and hexose sugars may be simultaneously or separately fermented to lactic acid using the microorganism of the present invention. If so desired, the hexoses may be fermented by a different microorganism to lactic acid, such as yeast, natural Lactobacillus, etc.

Many fermentation conditions are known per se as shown by the references mentioned in the Background of the Invention section above. Accordingly, the range of fermentation conditions may be quite broad. Likewise, any of the many known types of apparatus may be used for the present invention.

The microorganism according to the present invention may be used as a biologically pure culture or it may be used with other lactic acid producing microorganisms in mixed culture. Biologically pure cultures are generally easier to optimize but mixed cultures may be able to utilize additional substrates. One may also add enzyme(s) to the fermenter to aid in the degradation of substrates or to enhance lactic acid production. For example, cellulase may be added to degrade cellulose to glucose simultaneously with the fermentation of glucose to lactic acid by microorganisms. Likewise, a hemicellulase may be added to degrade hemicellulose.

In the preferred embodiment using a genetically engineered Lactobacillus, fermentation broth cultures are relatively resistant to contamination by other microorganisms. Nonetheless, it is preferred to eliminate or disable preexisting deleterious microorganisms in the substrate added to the Lactobacillus culture.

After fermentation, the lactic acid or lactate is separated from the fermentation broth by any of the many conventional techniques known to separate lactic acid or lactate from aqueous solutions. Particles of substrate or microorganisms may be removed before separation to enhance separation efficiency.

While the discussion of the fermentation in this specification generally refers to a batch process, parts or all of the entire process may be performed continuously. To retain the microorganisms in the fermenter, one may separate solid particles from the fluids. Alternatively, the microorganisms may be immobilized for retention in the fermenter or to provide easier separation.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are better illustrated by the use of the following non-limiting examples. The following examples are offered by way of illustration and not by way of limitation.

EXAMPLE 1
Demonstration of a Unique Inducible Pentose Phosphate Pathway in Lactobacillus MONT4

Lactobacillus MONT4, originally isolated from high-temperature fermenting grape musts (Barre, P. supra) was obtained from the German culture collection DSM (Mascheroder Weger 1B-33000 Braunschweig, Germany) under the designation DSM 20605. This microorganism is unique in that it ferments L-arabinose and D-ribose exclusively to lactic acid, apparently by a metabolic pathway unknown among other lactobacilli, which typically use the phosphoketolase pathway. Lactobacillus MONT4 was cultured at 37° C. for 18 hours in MRS broth (pH 6.7), containing 10 g/l proteose peptone no. 3 (Difco Laboratories); 10 g/l beef extract (Difco); 5 g/l yeast extract (Difco Laboratories); 1 g/l Tween 80 (Difco); 5 g/l sodium acetate $3H_2O$ (Sigma); 2 g/l dibasic potassium phosphate (Sigma); 2 g/l triammonium citrate (Sigma); 0.2 g/l magnesium sulfate$7H_2O$ (Sigma); 0.05 g/l manganese sulfate $4H_2O$ (Sigma); and either 20 g/l D-glucose (Sigma), D-xylose (Sigma) or L-arabinose (Sigma). Growth was monitored by measuring absorbance at 600 nm using a Beckman DU640 sprectrophotometer. The cells were collected by centrifugation, washed in 50 mM Tris-HCl pH 7.6 containing 1 mM DTT (TD), and resuspended in TD. Cell pellets were frozen at −80° C. until ready to use. Cell-free extracts were prepared and analyzed for the presence of xylose assimilation (xylose isomerase and xylulokinase) and pentose phosphate pathway enzymes (transaldolase and transketolase) as follows: the cells were thawed and ruptured using Aminco French Pressure Cell Press operated at 1000 psi gauge pressure or 20,000 psi cell pressure. Cell debris was removed by centrifugation (17,000×g, 30 min, 4° C.). Protein determinations were performed using the Bio-Rad Protein Assay, based on the Bradford dye-binding procedure (Bradford, M., *Anal. Biochem.* 72, p248, 1976), using BSA as the standard.

Xylose isomerase activity was measured by a modification of the cysteine-carbazole method (Schlief, R. F. and Wensink, P. C., *Practical Methods in Molecular Biology*, Enzyme Assays, pp. 46–50) in a reaction mixture containing 50 mM Tris-HCl (pH 7.6), 100 mM D-xylose and 20 mM $MnCl_2$. Cell-free extracts were diluted in 50 mM Tris-HCl (pH 7.6), added to an equal volume of reaction mix (100 μl total volume), and incubated for 10 minutes at 37° C. before the reaction was terminated by the addition of 900 μl of 0.1N HCl. 100 μl of freshly prepared 1.5%(w/v) cysteine-HCl, 100 μl of 0.12%(w/v)carbazole in 95% ethanol, and 3 ml of 70% sulfuric acid were added to the reaction mixture and the absorbance at 550 nm was measured after a 30 minute incubation at room temperature. The absorbance was compared to a linear standard curve prepared by using D-xylulose in the reaction mix. Units are measured as μmoles xylulose formed per minute per mg of protein. Xylulokinase activity was measured as described by Feldmann et. al., (*Mol. Gen. Genet.* 234, pp. 201–210, 1992).

Transaldolase and transketolase activities were measured by a modification of the methods described by Menezes et. al., (*Indian Journal of Biochemistry & Biophysics* 27, pp.18–22, 1990) and Feldmann et al., supra. The reaction mixture for the transketolase assay contained 50 mM Tris-HCl (pH 7.6), 10 mM $MgCl_2$, 1.1 mM erythrose-4-phosphate (Sigma), 1.1 mM co-carboxylase (TPP-Sigma), 0.2 mM xylulose-5-phosphate (Sigma), 3.6 units of phosphoglucose isomerase (Boehringher Mannheim), 0.2 units of glucose-6-phosphate dehydrogenase (Boehringher Mannheim), and 0.37 mg of NADP (Sigma) in a 500 μl volume. The reaction mixture for the transaldolase assay contained 50 mM Tris-HCl (pH 7.6), 20 mM EDTA, 1.1 mM D-sedoheptulose-7-phosphate (Sigma), 1.1 mM D,L-glyceraldehyde-3-phosphate from diethylacetal, monobarium salt (Sigma), 3.6 units of phosphoglucose isomerase, 0.2 units of glucose-6-phoshpate dehydrogenase, and 0.37 mg of NADP (Sigma) in a 500 µl volume. The formation of NADPH was monitored by absorbance at 365 nm over time. One unit of enzyme activity is defined as 1 µmole NADPH/minute/mg protein.

Xylose assimilation and pentose phosphate pathway enzyme activities were determined for Lactobacillus MONT4, grown in MRS media supplemented with either 2% glucose or 2% arabinose; L. casei rhamnosus (NRRL-B445), previously designated as L. delbrueckii delbrueckii, grown in MRS media supplemented with 2% glucose; and L. brevis (IFO 3960), grown in MRS media supplemented with either 2% glucose or 2% xylose. The facultative homofermentative L. casei rhamnosus (NRRL-B445) does not utilize xylose or contain a pentose phosphate pathway but metabolizes ribose via an inducible phosphoketolase pathway. In contrast, the obligate heterofermentative L. brevis (IFO 3960) metabolizes both hexose and pentose sugars, including xylose, via the phosphoketolase pathway and served as a positive control for measurement of both xylose isomerase and xylulokinase activities.

TABLE 1

Enzymatic Activities of Lactobacillus (µmoles/min-mg)

| Sample | Substrate | Xylose Isomerase | Xylulose Kinase | Trans-ketolase | Trans-aldolase |
|---|---|---|---|---|---|
| NRRL-B445 | glucose | <0 | 0.002 | 0.004 | 0.003 |
| MONT4 | glucose | <0 | 0.011 | 0.013 | 0.018 |
| MONT4 | arabinose | <0 | 0.006 | 0.200 | 0.172 |
| IFO 3960 | glucose | <0 | 0.006 | <0 | 0.031 |
| IFO 3960 | xylose | 1.099 | 0.028 | <0 | 0.016 |

The results shown in Table 1 demonstrate the presence of the transaldolase and transketolase activities characteristic of the non-oxidative portion of the pentose phosphate pathway in Lactobacillus MONT4 grown in the presence of arabinose. No significant transaldolase or transketolase activities were detected in either Lactobacillus MONT4 or L. casei rhamnosus grown in the presence of glucose, or in L. brevis grown in the presence of either glucose or xylose. These results demonstrate the presence of a unique inducible pentose phosphate pathway in Lactobacillus MONT4, previously unknown, which distinguishes Lactobacillus MONT4 from other lactobacilli in its ability to ferment a pentose sugar, such as arabinose, via an inducible pentose phosphate pathway. The results also indicate the absence of the xylose isomerase and xylulokinase activities necessary for xylose assimilation in Lactobacillus MONT4.

EXAMPLE 2

Development of a Xylose-Fermenting Strain of Lactobacillus MONT4

To develop a xylose-fermenting strain of Lactobacillus MONT4 suitable for fermentation of the xylose component in lignocellulosic feedstocks, Lactobacillus MONT4 was transformed with plasmid pLP3537-xyl (Posno et al., supra), containing the L. pentosus xylose operon by a modification of the procedure described by Posno et al. (Appl. Environ. Microbiol. 57, pp. 1822–1828, 1991). This modification is described in Example 3, below. To prepare competent cells, a log-phase culture of Lactobacillus MONT4 was diluted 1:1000 and grown overnight in MRS media (Difco) containing 2% (w/v) glucose. The cells were harvested by centrifugation at 7000 rpm for 15 minutes at 15° C. using a Sorval GSA rotor, washed twice with an equal volume of cold, sterile water and resuspended in 3 ml of sterile, cold 30% (v/v) PEG 1450 (Sigma). The cells were collected by centrifugation at 17,000×g for 2 minutes and resuspended in 30% (v/v) PEG 1450 to an approximate $OD_{600}$ of 45. For electroporation, 0.1 µg pLP3537-xyl in 5 µl of TE buffer was added to 50 µl of competent cells and the cells were electroporated in 0.2 cm cuvettes at 25 µF, 12.5 KV/cm, 200Ω using a BioRad Gene Pulser.

After electroporation, cells were incubated for 3–4 hours at 37° C. in MRS media containing 2% (w/v) glucose. Cell suspensions were then plated onto MRS agar (Difco) plates containing 2% (w/v) glucose and 10 µg/ml erythromycin and incubated at 37° C. for up to 5 days. Plasmid DNA from erythromycin-resistant transformants was isolated according to the procedure described by O'Sullivan and Klaenhammer, (Applied and Environmental Microbiology, 59, pp.2730–2733, 1993) using both mutanolysin (Sigma) and lysozyme (Sigma) to aid in cell lysis. Restriction analysis of the plasmid DNA isolated from erythromycin-resistant transformants confirmed the presence of pLP3537-xyl in Lactobacillus MONT4. Further analysis of the erythromycin-resistant transformants using API 50 CH strip tests (bioMerieux) also showed their sugar utilization patterns to be typical of Lactobacillus MONT4 prior to transformation with pLP3537-xyl, with the exception that transformants harboring pLP3537-xyl were also capable of growth on MRS agar plates containing 20 g/l D-xylose, 20 µg/ml erythromycin and 0.017% bromocresol purple. Transformants containing plasmid pLP3537-xyl demonstrated growth on xylose as the sole-carbon source and the formation of yellow halos surrounding colonies. This is the first example of genetic transformation of Lactobacillus MONT4 with heterologous DNA to create a xylose-fermenting strain of Lactobacillus MONT4.

To test the fermentation performance of Lactobacillus MONT4 (pLP3537-xyl), cells were inoculated into MRS broth containing either 20 g/l xylose, 20 g/l glucose or 10 g/l of both glucose and xylose and were incubated at 37° C. Growth was monitored by measuring the $OD_{600}$ using a Spectronic 601 spectrophotometer. Samples were taken at selected time intervals for measurement of sugar utilization and product formation. The presence of organic acids was determined by using a Hewlett Packard LC1090 HPLC equipped with an HP1047A RI detector and a Bio-Rad Aminex 300×7.8 mm HPX-87H ion exclusion column heated to 65° C. The mobile phase was 0.01N $H_2SO_4$ run at 0.6 ml/min.

Figure 1B:
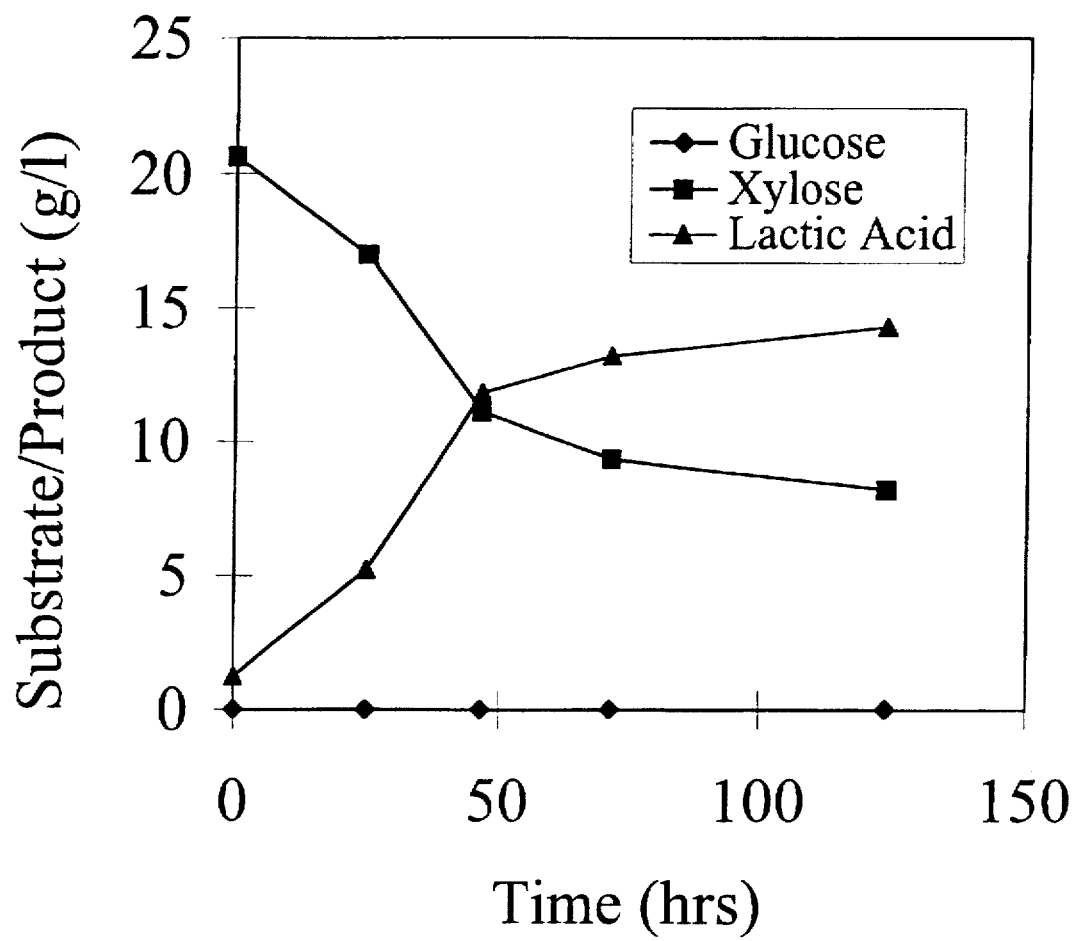
Figure 1C:
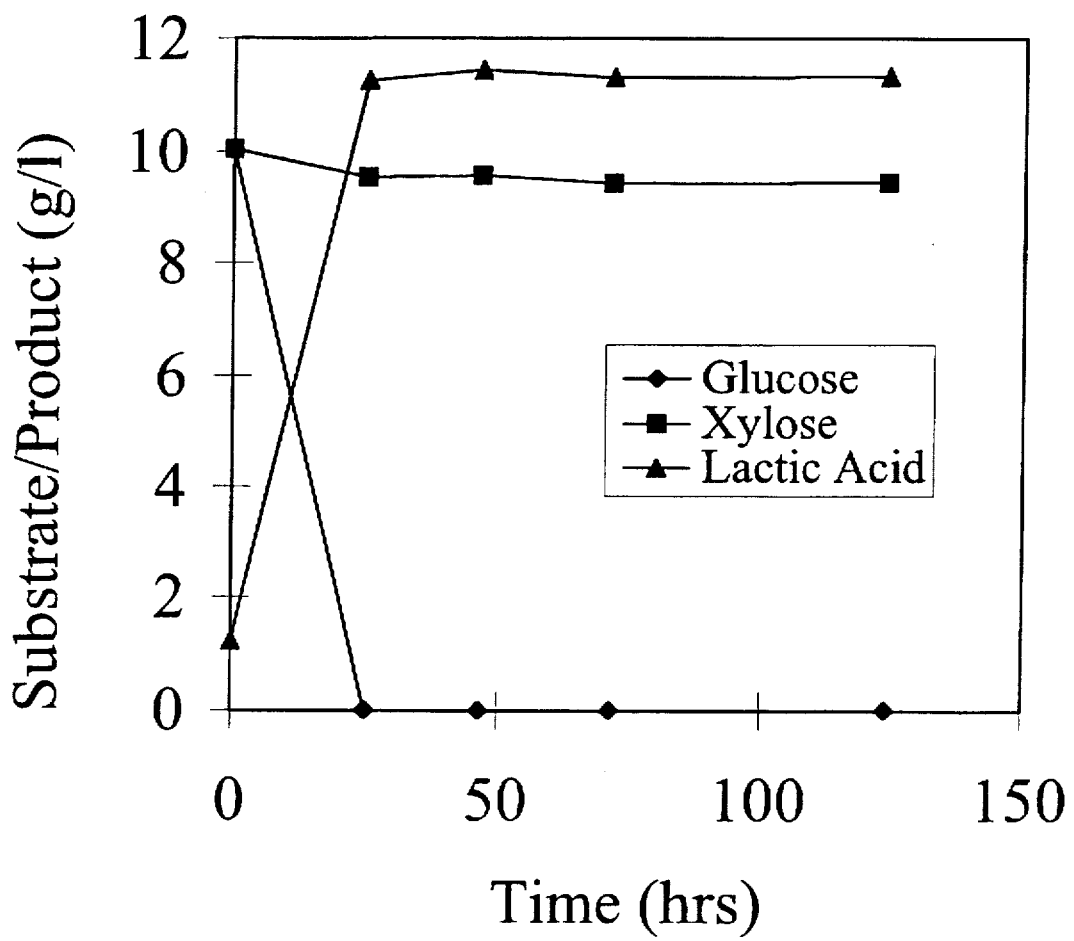

The results shown in FIG. 1 demonstrate the ability of Lactobacillus MONT4 (pLP3537-xyl) to ferment xylose to lactic acid at 94% of the maximum theoretical yield, based on the amount of consumed sugar. This is the first demonstration of a Lactobacillus with the ability to exclusively ferment xylose to lactic acid via the pentose phosphate pathway. The results also showed that only approximately 65% of the available xylose was consumed. In addition, xylose utilization was completely repressed in the presence of 1% (w/v) glucose. In contrast to the results previously reported for Lactobacillus MONT4 (Barre, P., supra), both Lactobacillus MONT4 and Lactobacillus MONT4 (pLP3537-xyl) consumed only approximately 65% of the available arabinose in MRS media containing 20 g/l L-arabinose after 96 hours at 37° C. Analysis of individual colonies from the original Lactobacillus MONT4 culture revealed two different cell types. Analysis of both types using API 50 CH strip tests revealed identical sugar utilization patterns. However, one type consistently consumed only approximately 65% of the available arabinose and at a slower rate compared to the other type. The strain demonstrating faster and complete arabinose consumption was demonstrating as Lactobacillus MONT4⁺ and was subsequently transformed with plasmid pLP3537-xyl as described above.

The fermentation performance of Lactobacillus MONT4⁺ (pLP3537-xyl) was determined in MRS media containing 10 µg/ml erythromycin and either 20 g/l D-glucose, 20 g/l D-xylose, 20 g/l L-arabinose, 10 g/l of both D-glucose and L-arabinose, 10 g/l of both D-glucose and D-xylose, or 10 g/l of both D-xylose and L-arabinose. Inocula were passaged twice in MRS media containing 10 µg/ml erythromycin and 20 g/l glucose, 20 g/l xylose or 20 g/l arabinose prior to inoculation of mid-log phase cells into fermentation media to an initial $OD_{600}$ of 0.08–0.1. Control fermentations were run with wild-type Lactobacillus MONT4⁺ for comparison to Lactobacillus MONT4⁺ (pLP3537-xyl), with the exception that erythromycin was not added to the controls. The cultures were incubated at 37° C. and growth was monitored by measuring the $OD_{600}$ over time using a Spectronic 601 spectrophotometer. Samples were taken at selected time intervals for measurement of sugar utilization and product formation. The conversion yields based on either sugar consumed in 143 hrs (Yp/s) or total available sugars (Yp) are summarized in Table 2.

TABLE 2

Conversion Yields with Lactobacillus MONT4⁺(pLP3537-xyl)

| Fermentation Substrate | Inocula Substrate | Yp | Yp/s |
|---|---|---|---|
| 2% Glucose | Glucose | 92% | 92% |
| 2% Xylose | Xylose | 86% | 98% |
| 2% Arabinose | Arabinose | 96% | 96% |
| 1% Xyl + 1% Ara | Xylose | 82% | 97% |
| 1% Xyl + 1% Ara | Arabinose | 84% | 99% |
| 1% Xyl + 1% Glu | Xylose | 49% | 93% |

The results presented in Table 2 show that the theoretical lactate yields based on the amount of consumed sugar (Yp/s) were greater than 92% for all sugars and mixtures of sugars tested. When grown in the presence of 2% xylose, Lactobacillus MONT4+ (pLP3537-xyl) utilized 86% of the total available xylose after 120 hours of incubation, an improvement over the approximately 65% lactate yields previously observed with Lactobacillus MONT4 (pLP3537-xyl). The presence of 1% glucose completely repressed xylose metabolism. When Lactobacillus MONT4+ (pLP3537-xyl) was grown in the presence of 1% xylose and 1% arabinose, all the available arabinose and approximately 65% of the available xylose was utilized after 24 hours and 144 hours, respectively.

EXAMPLE 3

Reduction of Glucose Catabolite Repression of Xylose Utilization

For an efficient industrial process, it is necessary to alleviate glucose catabolite repression of pentose assimilation. The expression of the wild-type L. pentosus MD353 xylAB operon is negatively regulated at the level of transcription by a repressor, the product of xylR, and transcribed from a different promoter (Lokman et. al., Mol. Gen. Genet. 245, pp.117–125, 1994). Thus, elimination of the xylR gene upstream of xylA might reduce glucose catabolite repression of the xylAB genes.

Therefore, a cloning strategy was designed to isolate the xylose isomerase (xylA) and xylulokinase (xylB) genes from the xylose operon contained on pLP3537-xyl by PCR synthesis followed by subcloning into the shuttle vector, pLP3537 (Leer et. al., Mol. Gen. Genet., 234, pp.265–274, 1992). By eliminating the gene for xylR, regulation of xylA and xylB transcription might be reduced or even eliminated. To this end, two oligonucleotides were constructed (Macromolecular Sequences) for gene amplification via PCR:

5'-Primer #1: CCA TCG ATG GTA CCG TCG ACG TTC TAG AAA GCG TTT AC (SEQ ID NO: 1)

3'-Primer #2: CCA TCG ATG GTA CCG TCG ACA AGA CAC GTA AAA AAT CGC (SEQ ID NO: 2)

The first 20 bases of each oligonucleotide were designed to include three restriction sites for ClaI, KpnI and SalI to facilitate subsequent subcloning. The sequence in bold letters of oligonucleotide #1 is complimentary to the 5'-DNA sequence upstream of the xylose isomerase gene (xylA). The DNA sequence for the L. pentosus xylose operon can be found in GenBank under the accession number M57384. The underlined sequence includes the –35 region of the promoter for xylAB. The sequence in bold letters for oligonucleotide #2 is the inverse complement of the sequence downstream of xylB and includes a potential transcription terminator. The PCR was performed with oligos #1 and #2 at 0.2 mM dNTP (Perkin Elmer) in a reaction volume of 0.1 ml containing 50 pg pLP3537-xyl, 0.2 mg/ml BSA (New England Biolabs), 2 units $Vent_R$ DNA Polymerase and buffer supplied by the manufacturer (New England Biolabs). Temperature cycling conditions were 1 min at 94° C., 2 min at 50° C. and 3 min at 72° C. for 25 cycles. The expected 3.2 kb DNA fragment, designated xylAB, was isolated by preparative agarose gel electrophoresis using Geneclean (BIO 101). However, repeated attempts to subclone xylAB into E. coli XL-1 Blue using a pCR-Script™SK(+) (Stratagene) as described by the manufacturer were unsuccessful. A single transformant was obtained, however DNA sequence analysis showed that 400 bases at the 5' end of the PCR product were deleted. The recovered plasmid, designated pBSxylAB, contained the 3' end of xylA and the entire xylB gene. Although the parent plasmid pLP3537-xyl could be successfully transformed into E. coli XL-1 Blue, the subcloning of xylAB into pCR-Script™SK(+) apparently resulted in a structurally unstable plasmid in E. coli.

Figure 2:
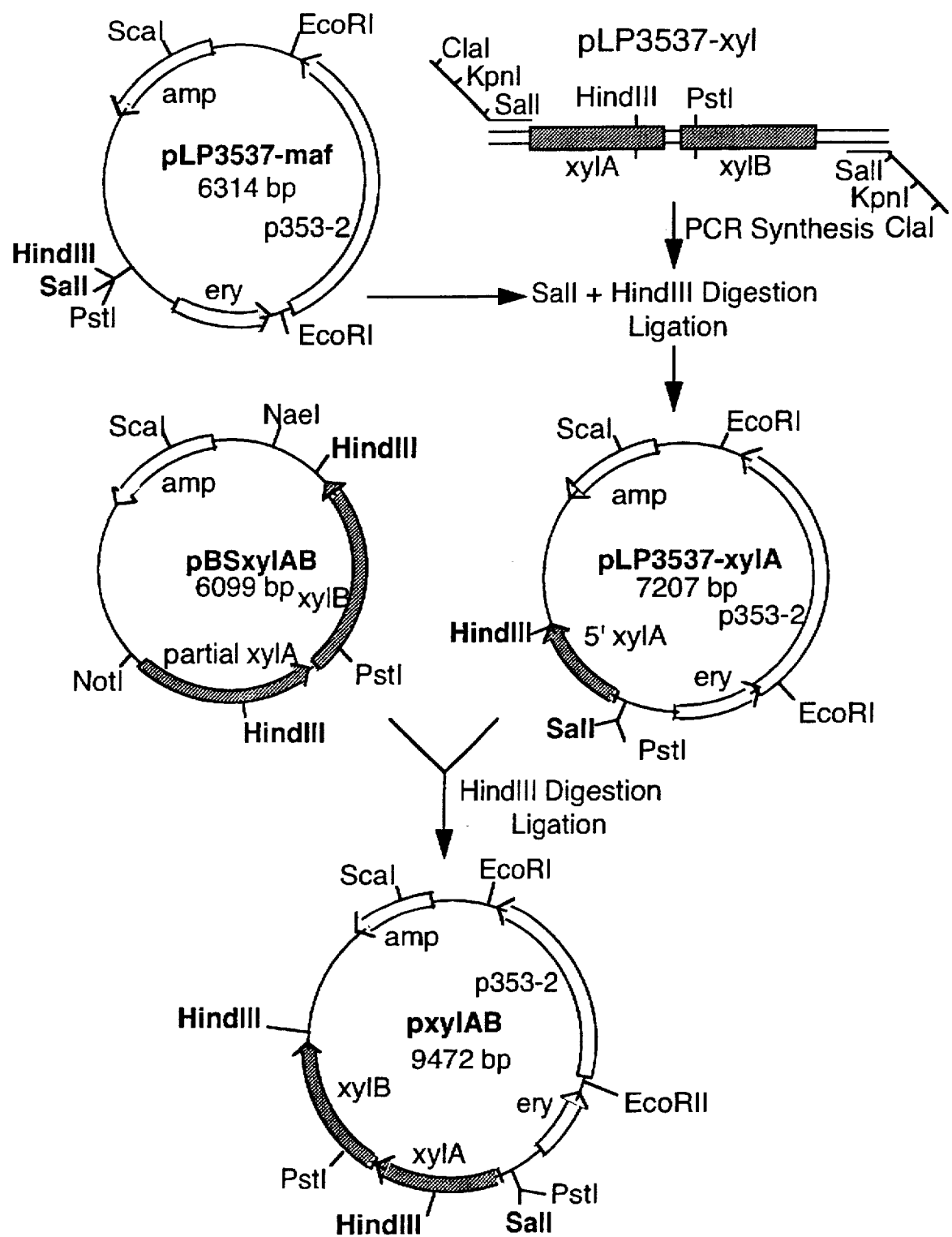
FIG. 2 is a series of plasmid maps showing the generation of pxylAB.

Therefore, a two-step cloning strategy was designed to first introduce the 5' end of xylA followed by the rest of the xylAB structural genes (FIG. 2). A modified plasmid was first constructed by removing the xylose operon from pLP3537-xyl by digestion with PstI and HindIII, and then religating the plasmid with two annealed oligonucleotides having PstI and HindIII overhangs and internal SalI and BglII restriction sites. The sequence for both oligonucleotides follows:

5' GGTCGACAGATCTA 3' (SEQ ID NO: 3)

5' AGCTTAGATCTGTCGACCTGCA 3' (SEQ ID NO: 4)

The resulting plasmid, designated pLP3537-maf, thus differs from pLP3537 (Posno, 1991, supra) by the addition of two restriction sites. The 5' end of xylA was then subcloned into pLP3537-maf as follows: the PCR product xylAB was digested with SalI and HindIII and the resulting 900 bp DNA fragment was purified by preparative agarose gel electrophoresis, ligated to pLP3537-maf previously digested with SalI and HindIII and dephosphorylated with calf intestinal phosphatase, and transformed into E. coli DH5α. The expected plasmid, designated pLP3537-xylA, was recovered from an ampicillin-resistant transformant. The remainder of xylA and xylB was then subcloned into pLP3537-xylA using a gel-purified 2.3 kb HindIII fragment obtained from digestion of pBS-xylAB. The ligation mixture was then transformed into *L. casei casei* 102S. The plasmid, designated pxylAB, was isolated from *L. casei casei* 102S and transformed into Lactobacillus MONT4$^+$. Restriction analysis of plasmid DNA isolated from erythromycin-resistant colonies confirmed the presence of the expected plasmid in Lactobacillus MONT4$^+$.

To determine whether removal of the regulatory gene, xylR, had an effect on xylose assimilation in the presence of glucose, Lactobacillus MONT4$^+$ (pxylAB) and Lactobacillus MONT4$^+$ (pLP3537-xyl), grown in the presence of either glucose or xylose, were inoculated to an initial OD600 of 0.08–0.1 into MRS media containing 10 µg/ml erythromycin and either 2% glucose, 2% xylose or 0.4% glucose+1.6% xylose. The cultures were incubated at 37° C. for up to 137 hrs. Growth, sugar utilization and product formation were monitored as described above.

TABLE 3

Lactate Yields after 137 hours

| Strain | Media | Inoculum | Yp | Yp/s |
|---|---|---|---|---|
| Mont4 + (pLP3537-xyl) | 2% glucose | glucose | 91% | 91% |
| Mont4 + (pxylAB) | 2% glucose | glucose | 93% | 93% |
| Mont4 + (pLP3537-xyl) | 2% xylose | xylose | 76% | 95% |
| Mont4 + (pxylAB) | 2% xylose | xylose | 82% | 101% |
| Mont4 + (pLP3537-xyl) | 0.4% glu + 1.6% xyl | glucose | 56% | 103% |
| Mont4 + (pxylAB) | 0.4% glu + 1.6% xyl | glucose | 74% | 99% |
| Mont4 + (pLP3537-xyl) | 0.4% glu + 1.6% xyl | xylose | 68% | 102% |
| Mont4 + (pxylAB) | 0.4% glu + 1.6% xyl | xylose | 80% | 99% |

The results presented in Table 3 demonstrate that improved lactate yields were obtained with MONT4+ (pxylAB) based on consumed sugar (Yp/s) and total available sugars (Yp) in MRS media containing either 2% (w/v) glucose or 2% (w/v) xylose. In contrast to Mont4+ (pLP3537-xyl), no lag in growth or in lactate production was observed with Mont4+ (pxylAB) in MRS media containing 0.4% glucose and 1.6% xylose after the glucose was consumed in about 40 hrs. Both strains demonstrated the highest lactate yields $Y_p$ in MRS media containing 2% (w/v) glucose, followed by 2% (w/v) xylose, 0.4% (w/v) glucose +1.6% (w/v) xylose (xylose inoculum), and 0.4% (w/v) glucose+1.6% (w/v) xylose (glucose inoculum). It is apparent from these results that the lactate yields based on total available sugars were greater with Lactobacillus MONT4+ (pxylAB), indicating that removal of xylR has improved xylose fermentation performance, either in the presence or absence of glucose.

Although the foregoing examples have been written with respect to specific embodiments, the spirit of the invention is not limited thereto and various modifications which would be obvious to one skilled in the art are intended to be encompassed herein as recited by the appended claims.

We claim:

1. A homofermentative microorganism Lactobacillus MONT4 containing exogenous genes encoding xylose isomerase and xylukokinase which functions with transaldolase and transketolase enzymes in the pentose phosphate pathway for homofermentating xylose to lactic acid, wherein the microorganism homofermentates xylose to lactic acid in high yields of 94% of maximum yield based upon an amount of consumed sugar and wherein said microorganism without said exogenous genes being incapable of homofermentating said xylose to lactic acid.

2. The microorganism of claim 1, containing exogenous genes encoding xylose isomerase and xylulokinase.

3. The microorganism of claim 2, wherein said genes encoding xylose isomerase and xylulokinase are obtained from *Lactobacillus pentosus*.

4. The microorganism of claim 1, wherein said genes are located on a vector.

5. The microorganism of claim 4, wherein said vector is a plasmid.

6. A vector containing genes encoding xylose isomerase and xylulokinase obtained form *Lactobacillus pentosus*, but not containing the xylR gene.

7. The vector of claim 6, wherein the vector is a plasmid.

8. A process of producing lactic acid or lactate in high yields from lignocellulosic biomass by adding the microorganism of claim 1 into said lignocellulosic biomass to ferment sugars to lactic acid or lactate.

9. The process according to claim 8 wherein the lignocellulosic biomass contains xylose.

10. The process according to claim 8 wherein the lignocellulosic biomass contains xylose and glucose.

11. The process according to claim 8 wherein the lignocellulosic biomass contains xylose, glucose and arabinose.

12. The microorganism of claim 11, wherein the transaldolase and transketolase are inducible in the presence of arabinose.

* * * * *

UNITED STATES PATENT AND TRADEMARK OFFICE
CERTIFICATE OF CORRECTION

PATENT NO. : 5,798,237
DATED : August 25, 1998
INVENTOR(S) : Stephen K. Picataggio et al.

It is certified that error appears in the above-identified patent and that said Letters Patent is hereby corrected as shown below:

On title page, item [73]

In the Assignee:

In line 2, change "Mich." to --Mo.--.

Signed and Sealed this

Sixth Day of April, 1999

*Attest:*

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PCR PRIMER"

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

CCATCGATGG TACCGTCGAC GTTCTAGAAA GCGTTAC        3 8

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear (ii) MOLECULE TYPE: other nucleic acid
            (A) DESCRIPTION: /desc = "PCR PRIMER"

(iii) HYPOTHETICAL: NO (iv) ANTI-SENSE: NO (v) FRAGMENT TYPE: C-terminal (xi) SEQUENCE DESCRIPTION: SEQ ID NO:2:

CCATCGATGG TACCGTCGAC AAGACACGTA AAAAATCGC                              39

(2) INFORMATION FOR SEQ ID NO:3:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (xi) SEQUENCE DESCRIPTION: SEQ ID NO:3:

GGTCGACAGA TCTA                                                          14

(2) INFORMATION FOR SEQ ID NO:4:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (xi) SEQUENCE DESCRIPTION: SEQ ID NO:4:

AGCTTAGATC TGTCGACCTG CA                                                 22